United States Patent
Urman et al.

(10) Patent No.: US 11,109,773 B2
(45) Date of Patent: Sep. 7, 2021

(54) TREATING PATIENTS WITH TTFIELDS WITH THE ELECTRODE POSITIONS OPTIMIZED USING DEFORMABLE TEMPLATES

(71) Applicant: Novocure Limited, St. Helier (JE)

(72) Inventors: Noa Urman, Pardes Hanna Carcur (IL); Zeev Bomzon, Kiryat Tivon (IL)

(73) Assignee: Novocure GmbH, Root (CH)

( * ) Notice: Subject to any disclaimer, the term of this patent is extended or adjusted under 35 U.S.C. 154(b) by 464 days.

(21) Appl. No.: 15/840,191

(22) Filed: Dec. 13, 2017

(65) Prior Publication Data

US 2018/0160933 A1 Jun. 14, 2018

Related U.S. Application Data (60) Provisional application No. 62/433,501, filed on Dec. 13, 2016.

(51) Int. Cl.
*A61B 5/055* (2006.01)
*A61N 1/04* (2006.01)
(Continued)

(52) U.S. Cl.
CPC ............ *A61B 5/055* (2013.01); *A61B 5/0042* (2013.01); *A61N 1/0476* (2013.01); *A61N 1/32* (2013.01);
(Continued)

(58) Field of Classification Search
None
See application file for complete search history.

(56) References Cited

U.S. PATENT DOCUMENTS 7,565,205 B2 7/2009 Palti
2005/0202384 A1* 9/2005 DiCuccio ............. G09B 23/285
434/262

(Continued)

FOREIGN PATENT DOCUMENTS

WO 2010120823 A2 10/2010

OTHER PUBLICATIONS

Kemmling et al. "Decomposing the Hounsfield Unit". Clin Neuroradiol (2012) 22:79-91. doi: 10.1007/s00062-011-0123-0 (Year: 2012).*
(Continued)

*Primary Examiner* — Amanda Lauritzen Moher
*Assistant Examiner* — Jillian K. McGough
(74) *Attorney, Agent, or Firm* — Potomac Law Group, PLLC (57) ABSTRACT

Embodiments receive images of a body area of a patient; identify abnormal tissue in the image; generate a data set with the abnormal tissue masked out; deform a model template in space so that features in the deformed model template line up with corresponding features in the data set; place data representing the abnormal tissue back into the deformed model template; generate a model of electrical properties of tissues in the body area based on the deformed and modified model template; and determine an electrode placement layout that maximizes field strength in the abnormal tissue by using the model of electrical properties to simulate electromagnetic field distributions in the body area caused by simulated electrodes placed respective to the body area. The layout can then be used as a guide for placing electrodes respective to the body area of the patient to apply TTFields to the body area.

22 Claims, 6 Drawing Sheets

(51) Int. Cl.

| | | |
|---|---|---|
| A61B 5/00 | (2006.01) | |
| A61N 1/32 | (2006.01) | |
| A61N 1/40 | (2006.01) | |
| A61N 1/36 | (2006.01) | |
| G16H 20/40 | (2018.01) | |
| G16H 50/20 | (2018.01) | |
| G16H 30/40 | (2018.01) | |
| G16H 50/50 | (2018.01) | |
| G06F 30/20 | (2020.01) | |
| G16H 50/00 | (2018.01) | |
| A61B 5/053 | (2021.01) | |
| A61N 1/05 | (2006.01) | |
| A61N 1/08 | (2006.01) | |

(52) U.S. Cl.
CPC ..... *A61N 1/36002* (2017.08); *A61N 1/36025* (2013.01); *A61N 1/40* (2013.01); *G06F 30/20* (2020.01); *G16H 20/40* (2018.01); *G16H 30/40* (2018.01); *G16H 50/20* (2018.01); *G16H 50/50* (2018.01); *A61B 5/053* (2013.01); *A61B 2576/026* (2013.01); *A61N 1/0456* (2013.01); *A61N 1/0529* (2013.01); *A61N 1/08* (2013.01); *G16H 50/00* (2018.01)

(56) References Cited

U.S. PATENT DOCUMENTS

| | | | | |
|---|---|---|---|---|
| 2009/0281415 | A1* | 11/2009 | Cupps | A61B 5/055 600/410 |
| 2013/0218157 | A1* | 8/2013 | Callas | A61B 18/14 606/41 |
| 2013/0226542 | A1* | 8/2013 | Rapaka | G06K 9/6207 703/2 |
| 2015/0088120 | A1* | 3/2015 | Garcia | C12N 13/00 606/34 |
| 2015/0174418 | A1 | 6/2015 | Tyler et al. | |
| 2016/0055304 | A1 | 2/2016 | Russell et al. | |
| 2017/0120041 | A1 | 5/2017 | Wenger et al. | |

OTHER PUBLICATIONS

Kotu et al. "Probability mapping of scarred myocardium using texture and intensity features in CMR images". BioMedical Engineering OnLine 2013, 12:91. p. 1-19. (Year: 2013).*

Wenger et al. "The electric field distribution in the brain during TTFields therapy and its dependence on tissue dielectric properties and anatomy: a computational study". 2015 Phys. Med. Biol. 60 7339-7357. doi:10.1088/0031-9155/60/18/7339 (Year: 2015).*

Ashburner et al., "Unified segmentation," NeuroImage, vol. 26, pp. 839-851, Apr. 2005.

Basser et al., "MR Diffusion Tensor Spectroscopy and Imaging," vol. 66, pp. 259-267, Jan. 1994.

Holmes et al., "Enhancement of MR Images Using Registration for Signal Averaging," Journal of Computer Assisted Tomography, vol. 22, Issue 2, pp. 324-333, Mar.-Apr. 1998.

International Search Report and Written Opinion issued in application No. PCT/IB2017/057901, dated Aug. 20, 2018.

Menze et al., "The Multimodal Brain Tumor Image Segmentation Benchmark (BRATS)," IEEE Transactions on Medical Imaging, IEEE, p. 1993-2024, 2014.

Michel et al., "Electrical conductivity and permittivity maps of brain tissues derived from water content based on T1-weighted acquistions," Magnetic Resonance in Medicine, vol. 77, Issue 3, pp. 1094-1103, Mar. 2017.

Miranda et al., "Predicting the electric field distribution in the brain for the treatment of glioblastoma," Physics in Medicine & Biology, vol. 59, pp. 4137-4147, Jul. 2014.

Porz et al., "Multi-Modal Glioblastoma Segmentation: Man versus Machine," PLOS One, vol. 9, No. 5, e96873, May 2014.

Segars et al., "4D XCAT phantom for multimodality imaging research," Med. Phys., vol. 37, No. 9, pp. 4902-4915, Sep. 2010.

Thielscher et al., "Field Modeling for transcranial magnetic stimulation: A useful tool to understand the physiological effects of TMS?," Conference Proceedings Annual International Conference of IEEE, pp. 222-225, Aug. 2015.

Timmons et al., " End-to-end workflow for finite element analysis of tumor treating fields in glioblastomas," Physics in Medicine and Biology, vol. 62, pp. 8264-8282, Oct. 2017.

Wenger et al., "Improving Tumor Treating Fields Treatment Efficacy in Patients with Glioblastoma Using Personalized Array Layouts," International Journal of Radiation Oncology Biology Physics, vol. 94, No. 5, pp. 1137-1143, 2016.

Wenger et al., "The electric field distribution in the brain during TTFields therapy and its dependence on tissue dielectric properties and anatomy: a computational study," Physics in Medicine and Biology, vol. 60, pp. 7339-7357, Sep. 2015.

Woo et al., "Reconstruction of High Resolution Tongue Volumes from MRI," IEEE Trans. Biomed. Eng., vol. 59, No. 12, pp. 3511-3524, Dec. 2012.

Woods et al., "A technical guide to tDCS, and related non-invasive brain stimulation tools," Clin. Neurophysiol., vol. 127, No. 2, pp. 1031-1048, Feb. 2016.

Yushkevich et al., "User-guided 3D active contour segmentation of anatomical structures: Significantly improved efficiency and reliability," NeuroImage, vol. 31, pp. 1116-1128, Mar. 2006.

Zhuang et al., "A Nonrigid Registration Framework Using Spatially Encoded Mutual Information and Free-Form Deformations," IEEE Transcations on Medical Imaging, vol. 30, Issue 10, pp. 1819-1828, Oct. 2011.

* cited by examiner

TREATING PATIENTS WITH TTFIELDS WITH THE ELECTRODE POSITIONS OPTIMIZED USING DEFORMABLE TEMPLATES

CROSS REFERENCE TO RELATED APPLICATIONS

This Application claims the benefit of U.S. Provisional Application 62/433,501 (filed Dec. 13, 2016) which is incorporated herein by reference in its entirety.

BACKGROUND

The use of electric fields and currents for treating neurological disorders and brain disease is becoming widespread. Examples of such treatments include, but are not limited to: Trans-cranial Direct Current Stimulation (TDCS), Transcranial Magnetic Stimulation (TMS), and Tumor Treating Fields (TTFields). These treatments rely on delivery of low-frequency electromagnetic fields to target regions within the brain. See, for example, Woods et. al., Clinical Neurophysiology, 127 1031-1048 (2016), which reviews technical aspects of TDCS; and Thielscher et. al., Conference Proceedings, Institute of Electrical and Electronics Engineers (IEEE), Engineering in Medicine and Biology Society, 222-225 (2015), which teaches methods for simulating TMS. As yet another example, Miranda et. al., Physics in Medicine and Biology, 59, 4137-4147 (2014), teaches the creation of a computational head model of a healthy individual for simulating delivery of TTFields using a magnetic resonance imaging (MRI) dataset, where model creation is performed in a semi-automatic manner. Further, Wenger et. al., Physics in Medicine and Biology, 60 7339-7357 (2015), teaches a method for creating a computational head model of a healthy individual for simulating delivery of TTFields, where the model is created from MRI datasets of a healthy individual.

In the case of TDCS and TMS, the treatment entails delivery of the electromagnetic fields to target regions in the brain in which they stimulate specific neurons. In the case of TTFields, the position of the transducer arrays on the patient's head is optimized to deliver maximal field intensity to the region of the tumor. See, for example, Wenger et. al., International Journal of Radiation Oncology•Biology•Physics, 941137-43 (2016), which teaches how Diffusion Tensor Imaging (DTI) data can be incorporated into models for simulating delivery of TTFields to the head. The DTI data is used to derive anisotropic conductivity tensors for each voxel in the head model.

TTFields are low intensity (e.g., 1-3 V/cm) alternating electric fields within the intermediate frequency range (100-300 kHz), which may be used, for example, to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed patients. These alternating electric fields are induced non-invasively by transducer arrays (i.e., arrays of capacitively coupled electrodes) placed directly on the patient's scalp (e.g., using the Novocure Optune™ system). TTFields also appear to be beneficial for treating tumors in other parts of the body.

In-vivo and in-vitro studies show that the efficacy of TTFields therapy increases as the intensity of the electric field increases in the target region, and the intensity in the target region is dependent on the placement of the transducer arrays on the patient's scalp.

One way to optimize the placement of the transducer arrays is to use a computer simulation. The use of a computer is necessary due to the large amount of imaging data that is processed and the simulation/optimization process being computationally-intensive and complex as described herein. Typically, when performing simulations, an anatomically accurate computational model is constructed, and electric properties are assigned to the various tissue types. Once the model has been constructed, simulated model electrodes are positioned on the model of the head and appropriate boundary conditions such as voltage on the electrodes are applied. The electric field within the head is then calculated. Using various computer-implemented and computationally-intensive optimization schemes, it is then possible to find the layout of electrodes and the boundary conditions that yield optimal electromagnetic field distributions within the head (and specifically, the target regions). However, individual patients vary in the details of their anatomy, and these variations influence the field distribution within the head of the individual. Therefore, in order to use simulations to optimize treatments involving the delivery of electromagnetic fields to target regions, it has heretofore been necessary to construct a personalized computational model for each individual.

A conventional approach for forming a head model is as follows. First, a set of medical images is acquired. Typically, the images include MRI and/or Computed Tomography (CT) images. Next, the images are segmented to determine which portions of the images correspond to each of the different possible tissue types (e.g., white matter, grey matter, cerebrospinal fluid (CSF), skull, etc.). Next, a series of meshes for each tissue type in the segmented image are constructed and incorporated into the model, and representative conductivity values are assigned to each tissue type. Finally, the electrodes are positioned on the model and the field distribution is solved using an appropriate numerical technique such as a finite elements method or a finite differences method (based on the positions in 3D space of the various tissue types and the conductivities assigned to each of those tissue types).

Although many steps in the process described above are implemented by a computer, the process still requires a great deal of human intervention because automatic algorithms for segmentation of medical images of a head, especially images in which tumors are present, are not robust and often require user intervention to obtain reliable results. See, for example, Menze et. al., IEEE Transactions on Medical Imaging, 34 1993-2024 (2014), which investigates performance of multiple algorithms for automatic segmentation of tumors. In addition, mesh regularization is a time-consuming process that requires user supervision, as described, for example, in Miranda et. al., Physics in Medicine and Biology, 59, 4137-4147 (2014), Wenger et. al., Physics in Medicine and Biology, 60 7339-7357 (2015), and Wenger et. al., International Journal of Radiation Oncology•Biology•Physics, 941137-43 (2016). Specifically, when creating a finite element model of a volume, the volume is meshed into volumetric elements. In order to ensure conversion of the numerical solution, it is desirable that the quality of all elements is high (with the definition of quality varying depending on the type of mesh being created). In addition, it is important to verify that elements do not intersect, and that in general the quality of the mesh is sufficient. Regularization is a process in which a mesh is processed to improve the conditioning of its elements and its overall quality. For a basic discussion, see S. Makarow et. al., "Low Frequency Electromagnetic Modelling For Electrical and Biological systems Using Matlab", John Wiley and Sons, 2010, pp. 36-81.

Between the segmentation and the mesh regularization, the man-hours required to create a single model can vary from hours to days, depending on the quality of the images and the complexity of the model being created.

SUMMARY OF THE INVENTION

One aspect of the invention is directed to a first method for improving treatment of a tumor using Tumor Treating Fields (TTFields). The first method includes receiving, by a processor of a computer system, a three-dimensional image of a body area of a patient, identifying portions of the image that correspond to abnormal tissue, and generating a data set corresponding to the image with the abnormal tissue masked out. The first method further includes retrieving a model template from a memory device of the computer system, the model template comprising tissue probability maps that specify positions of a plurality of tissue types in a healthy version of the body area of the patient, and deforming the model template in space so that features in the deformed model template line up with corresponding features in the data set. The first method also includes modifying portions of the deformed model template that correspond to the masked-out portion of the data set so that the modified portions represent the abnormal tissue, and generating a model of electrical properties of tissues in the body area based on (a) the positions of the plurality of tissue types in the deformed and modified model template and (b) the position of the abnormal tissue in the deformed and modified model template. The first method further includes determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets. The first method also includes placing the electrodes respective to the body area of the patient based on the determined electrode placement layout; and using the placed electrodes to apply TTFields to the body area.

Another aspect of the invention is directed to a second method for improving an electrotherapeutic treatment. The second method includes receiving, by a processor of a computer system, a three-dimensional image of a body area of a patient, identifying portions of the image that correspond to abnormal tissue, and generating a data set corresponding to the image with the abnormal tissue masked out. The second method also includes retrieving a model template from a memory device of the computer system, wherein the model template specifies positions of a plurality of tissue types in a healthy version of the body area of the patient, and deforming the model template in space so that features in the deformed model template line up with corresponding features in the data set. The second method further includes modifying portions of the deformed model template that correspond to the masked-out portion of the data set so that the modified portions represent the abnormal tissue, and generating a model of electrical properties of tissues in the body area based on (a) the positions of the plurality of tissue types in the deformed and modified model template and (b) the position of the abnormal tissue in the deformed and modified model template. The second method further includes determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets. The second method also includes outputting the determined electrode placement layout for subsequent use as a guide for placing electrodes respective to the body area of the patient prior to use of the electrodes for electrotherapeutic treatment.

In some embodiments of the second method, the deforming of the model template includes determining a mapping that maps the data set to a coordinate space of the model template, and applying an inverse of the mapping to the model template. Optionally, in these embodiments, the mapping is determined for points in the data set that fall outside of the masked-out portion. Optionally, in these embodiments, the model template comprises tissue probability maps, wherein the mapping maps the data set to the tissue probability maps.

Optionally, in these embodiments, the tissue probability maps are derived from images of a healthy individual from whom the model template has been derived. Optionally, in these embodiments, the tissue probability maps are derived by simultaneously registering and segmenting the images of the healthy individual using existing tissue probability maps, and wherein the existing tissue probability maps are derived from images of multiple individuals.

Optionally, in these embodiments, the tissue probability maps are existing tissue probability maps derived from images of multiple individuals.

Optionally, in these embodiments, the inverse of the mapping is applied to each one of the tissue probability maps, wherein the inverse-mapped tissue probability maps are combined into a segmented image comprising the deformed model template. Optionally, in these embodiments, combining the inverse-mapped tissue probability maps includes assigning to each voxel the tissue type which has the highest probability of occupying that voxel across the inverse-mapped tissue probability maps. Optionally, in these embodiments, combining the inverse-mapped tissue probability maps includes using a look-up table to assign a tissue type to each voxel that is assigned more than one tissue type across the inverse-mapped tissue probability maps.

In some embodiments of the second method, the identifying of the portions of the image that correspond to the abnormal tissue comprises performing segmentation of the image. In some embodiments of the second method, the model of electrical properties of tissues comprises a model of electrical conductivity or resistivity. In some embodiments of the second method, the image comprises an MRI image, a CT image, or a combination of MRI and CT images. In some embodiments of the second method, the body area comprises a head of the patient. In some embodiments of the second method, the portions of the image that correspond to the abnormal tissue correspond to a tumor. In some embodiments of the second method, the electrotherapeutic treatment comprises TTFields.

In some embodiments of the second method, the determining of the electrode placement layout comprises applying a boundary condition to the simulated electrodes in each one of at least two electrode placement layouts, solving a field distribution in the body area for each one of the at least two electrode placement layouts, and choosing the electrode placement layout that yields the strongest field within the abnormal region. Optionally, in these embodiments, the boundary condition corresponds to voltages or currents applied to the simulated electrodes.

In some embodiments of the second method, the model template is selected from a plurality of model templates based on similarities between the image and each of the model templates.

Some embodiments of the second method further include placing the electrodes respective to the body area of the patient based on the determined electrode placement layout, and using the electrodes to apply TTFields to the body area.

Another aspect of the invention is directed to an electrotherapeutic treatment device comprising a processor configured to execute instructions stored in one or more memory devices to perform an electrotherapeutic treatment. In these embodiments, the treatment includes receiving, by the processor, a three-dimensional image of a body area of a patient, identifying portions of the image that correspond to abnormal tissue, and generating a data set corresponding to the image with the abnormal tissue masked out. The treatment further includes retrieving a model template from the one or more memory devices, wherein that the model template specifies positions of a plurality of tissue types in a healthy version of the body area of the patient, deforming the model template in space so that features in the deformed model template line up with corresponding features in the data set, and modifying portions of the deformed model template that correspond to the masked-out portion of the data set so that the modified portions represent the abnormal tissue. The treatment further includes generating a model of electrical properties of tissues in the body area based on (a) the positions of the plurality of tissue types in the deformed and modified model template and (b) the position of the abnormal tissue in the deformed and modified model template. The treatment further includes determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets. The treatment also includes outputting the determined electrode placement layout for subsequent use as a guide for placing electrodes respective to the body area of the patient prior to use of the electrodes for electrotherapeutic treatment.

DETAILED DESCRIPTION OF THE PREFERRED EMBODIMENTS

The embodiments described herein generate a customized realistic head model for each individual patient by applying a non-rigid deformation to a preexisting realistic head model template, thus reducing the time and human labor required to create the head model. After the customized head model is generated for each individual patient, conventional simulation approaches are used to determine the optimal position for the transducer on the patient's body. Optionally, the pre-existing realistic head model template for the healthy patient may include tissue probability maps (TPMs). TPMs provide a model in which each point is represented by respective probabilities of that point belonging to various tissue types such as white matter, grey matter, CSF, etc.

Optionally, the patient images may be supplemented with other MRI data such as Diffusion Tensor Imaging (DTI) data or Water Content Electric Impedance Tomography (Wept) data to obtain more accurate representations of the conductivity in the patient's head, for example, as disclosed by E. Michel, D. Hernandez, and S. Y. Lee, "Electrical conductivity and permittivity maps of brain tissues derived from water content based on T 1-weighted acquisition," Magnetic Resonance in Medicine, 2016. MRI imaging techniques such as DTI or Wept are known to provide information on tissue conductivity as disclosed, for example, in U.S. application Ser. No. 15/336,660, which is incorporated herein by reference in its entirety.

Figure 1:
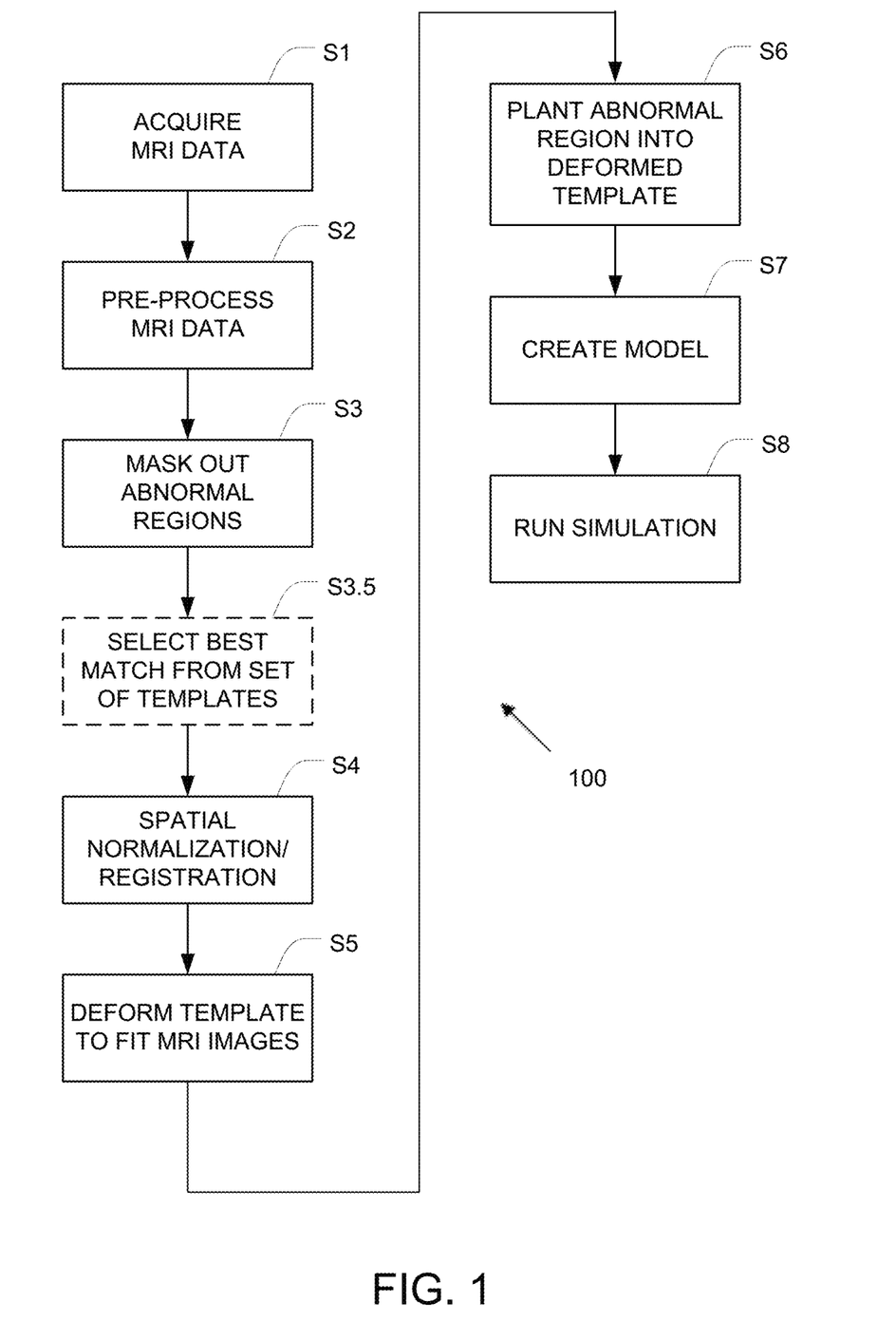
FIG. 1 is a flowchart of an embodiment that performs electrotherapeutic treatment by creating a realistic head model of a patient using a deformable template.
Figure 8:
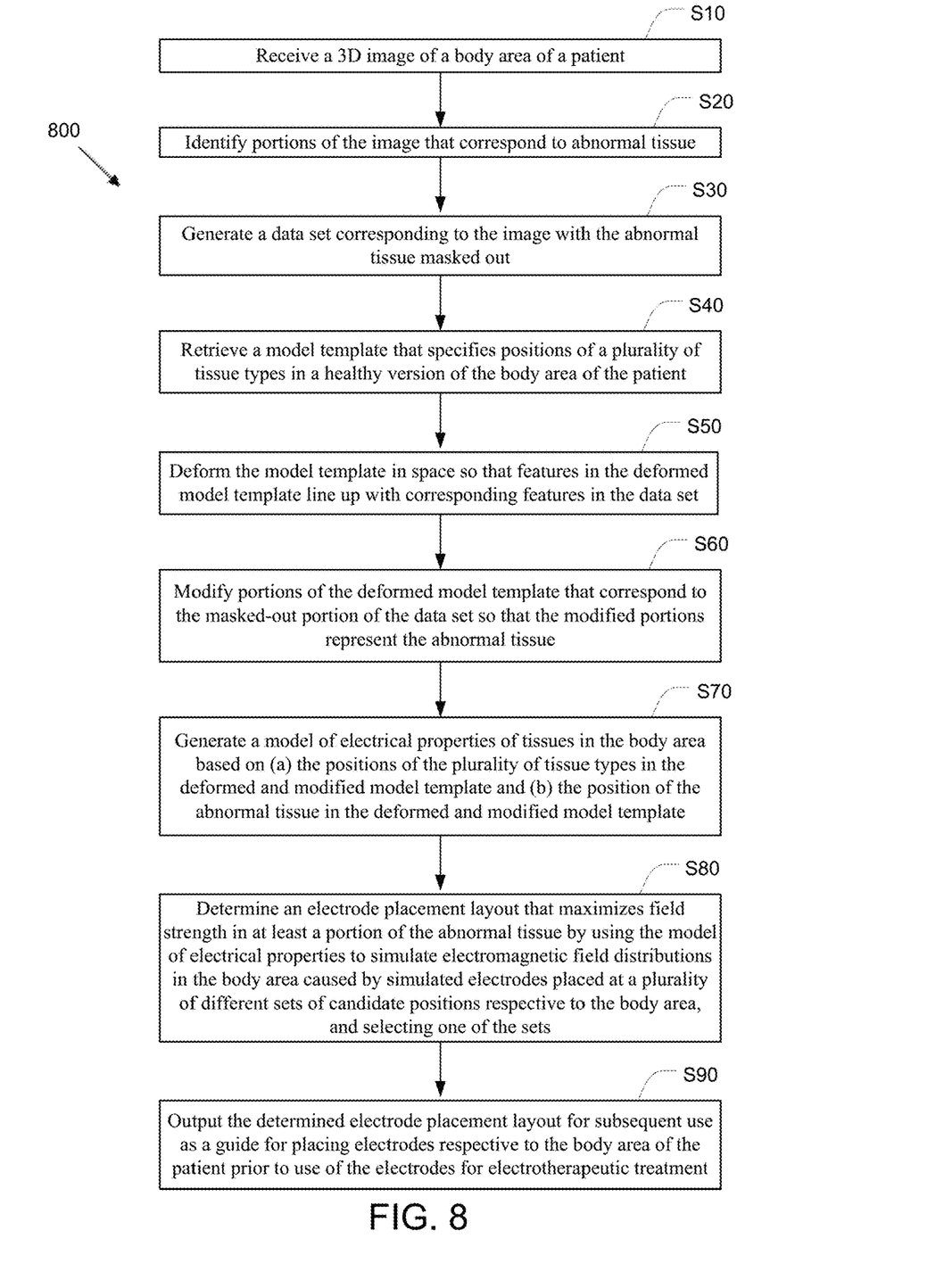
FIG. 8 is another flowchart of an embodiment that performs electrotherapeutic treatment by creating a realistic head model of a patient using a deformable template.

The FIG. 1 and FIG. 8 embodiments describes work-flows for creating an individualized realistic head model for each patient with reduced user intervention, and using these head models to optimize Tumor Treating Fields (TTFields) array layouts on patients. Once a realistic model has been constructed for any given patient, the optimization can be performed in a fully automatic or semi-automatic manner using a sequence of algorithms that is also described herein. Although these workflows are described in the context of TTFields they may also be used in alternative contexts.

The FIG. 1 and FIG. 8 embodiments begin with a deformable template that is a realistic head model of a healthy individual (as opposed to a realistic head model of the actual patient). This head model may be obtained using any conventional approach. For example, the realistic head model may be created in a standard coordinate system such as Montreal Neurological Institute (MNI) or Talairach spaces. For example, Holmes et. al., Journal of Computer Assisted Tomography, 22 324-333 (1998), which is incorporated herein by reference, teaches mapping and averaging of MRI images in the standard space of MNI. If the model does not exist in a desired standard coordinate space, the transformation from a standard coordinate space to the head model is preferably known and can be used to map the model to the standard coordinate space. One example of a realistic head model built in a standard coordinate space is the model based on the COLIN27 dataset (as described in Holmes et. al., Journal of Computer Assisted Tomography, 22 324-333 (1998)) created by Miranda et. al. (as described in Miranda et. al., Physics in Medicine and Biology, 59, 4137-4147 (2014), which is incorporated herein by reference). But a wide variety of alternative realistic head models for the healthy individual may be used in place of the Miranda model. It is desirable that the MRIs from which the model was created are also available for purposes that will be described hereinafter.

In some embodiments, the realistic head model template of the healthy individual provides TPMs of tissue types. That is, each point in the model is represented by respective probabilities of that point belonging to various tissue types such as white matter, grey matter, CSF, etc. In some embodiments, the realistic head model template of the healthy individual provides one TPM per tissue type (e.g., 6 TPMs for 6 tissue types of white matter, grey matter, skull, scalp, CSF, and air).

FIG. 1 describes a process 100 for using the realistic head model of the healthy individual to create a realistic head model for any given patient by using the existing head model as a deformable template.

The process 100 begins in step S1, which is the acquisition of an appropriate set of MRI images. In step S1 an MRI data set for an individual patient is acquired using any conventional approach. This data set preferably includes MRIs carrying structural data (such as that obtained from T1 or T2 MRI sequences). Optionally, additional sequences may also be acquired such as DTI or perfusion imaging that may carry additional information that could be useful for model creation as will be described hereinafter. In some instances, the parameters of the MRI sequences are optimized to increase contrast between specific tissue types. Enhancing contrast is useful for the image segmentation that follows in the steps described below, for example, as in the sequence described in Windhoff et. al., Human Brain Mapping, 34 923-935 (2013), which is incorporated herein by reference.

Preferably, the MRIs are acquired at the highest resolution that is practically possible. Usually, resolution of better than 1 mm×1 mm×1 mm is desired. However, images with lower resolution can also be used.

Optionally, DTI or Diffusion-weighted magnetic resonance imaging (DWI) data are acquired as well. This data can be used to map the conductivity (or conductivity tensor) within each voxel as described in Wenger et. al., International Journal of Radiation Oncology•Biology•Physics, 941137-43 (2016), and Basser et. al., Biophysical Journal, 66 259-267 (1994), which are incorporated herein by reference. In alternative embodiments, different imaging modalities may be used in place of MRI images, such as CT images, a combination of MRI and CT images, etc.

Figure 2:
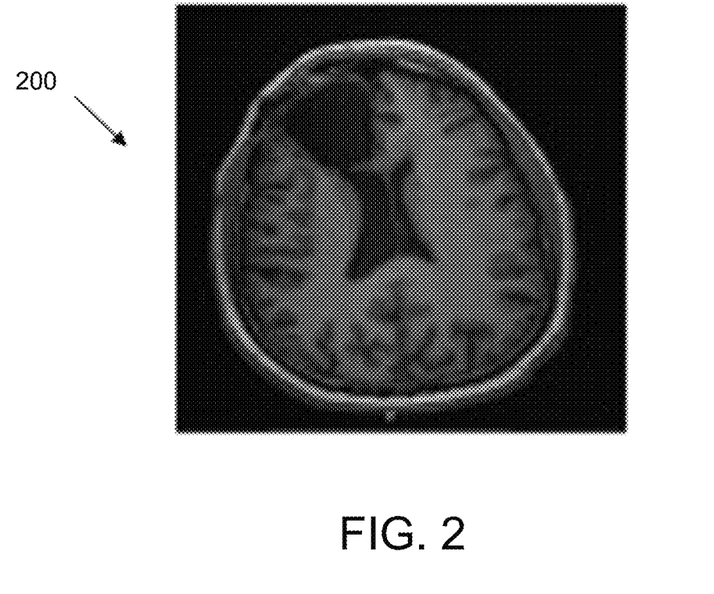
FIG. 2 depicts an original MRI image obtained from a patient with an abnormality (e.g., a tumor).

Process 100 continues in Step S2, which is image pre-processing. However, in some cases, no pre-processing is needed and Step S2 may be skipped. In step S2, image pre-processing is performed on the data obtained in step S1 to obtain a cleaner image. FIG. 2 shows an example of an MRI image 200 resulted after performing image pre-processing in step S2. The pre-processing may be implemented using any conventional approach. In some embodiments, the image pre-processing step includes image alignment and distortion correction. For example, image alignment may be implemented to remove artifacts due to motion from the images using any conventional approach. Re-alignment may be performed using affine registration, using any suitable conventional approach such as Statistical Parametric Mapping (SPM) as implemented in SPM 8.0 toolbox that is developed for the construction and assessment of spatially extended statistical processes used to test hypotheses about functional imaging data. In addition, distortion to the images (e.g., caused by induced eddy currents) may be corrected at this stage. Realignment of images is required when more than one dataset is used to create the models, in which case those multiple datasets need to be aligned. For example, when axial and coronal image sets are used for super resolution, they need to be aligned. As another example, when DTI data is used in addition to T1 data, DTI data and T1 data may need to be aligned.

In some embodiments, an additional pre-processing step of manipulating the header of the MRI image is performed (e.g., in Neuroimaging Informatics Technology Initiative (NifTI) format), so that the origin of the file matches the origin of the template TPM. The origin of the file refers to the origin of axes in the file. This step helps facilitate registration of the MRI image into the deformable space as described in step S4 below. In some embodiments, the origin of axes in the patient MRI images and in the files associated with the deformable template are positioned at similar voxels to help facilitate execution of step S4.

Optionally, super-resolution algorithms that combine several MRI datasets of a single patient into a single image may be used. These algorithms are useful for creating a dataset that shows the full head of the patient, when all other datasets truncate the head at different points, or for creating an image with high-resolution (or slice spacing) when the original data is of lower resolution. High-resolution datasets, and datasets that show the full 3D head are useful for creating an accurate head model. One example of a super-resolution algorithm is described in Woo, et al. "Reconstruction of high-resolution tongue volumes from MRI." IEEE Transactions on Biomedical Engineering, 59.12 (2012). This algorithm employed a number of pre-processing steps including motion correction and intensity normalization, followed by a region-based maximum a posteriori (MAP) Markov random field (MRF) approach to combine three orthogonal image volumes of MRI datasets into a single super-resolution isotropic volume reconstruction of the tongue. The output super-resolution image was superior to the input images in terms of both signal-to-noise ratio (SNR) and resolution.

In many cases, background noise and aliasing may be present and may deteriorate the quality of the head model created using deformable templates. In particular, when background noise is present, the contour of the skull obtained during model creation is often inaccurate and includes part of the background. Accordingly, some embodiments may implement various thresholding schemes known to persons skilled in the relevant arts to remove background noise and aliasing. Aliasing as referred herein relates to an artifact in MRI images that results in a weak "shadow" of the subject being imaged to appear in the background (i.e., the shadow is caused by aliasing). The shadow is typically upside down and directly attached to the main image. In this case, a thresholding scheme may be used to remove the weak shadow in the background. One example of a thresholding scheme that may be used to enhance image quality is a semi-automatic method in which the user selects a single value representing the background noise and the software applies this value as a threshold to automatically detect the contour of the scalp and zero the intensity of the background noise slice by slice. A wide variety of alternative approaches may also be used, as will be appreciated by persons skilled in the relevant arts.

Alternatively or additionally, scanner-specific pre-processing may be applied. For example, images may be converted from Digital Imaging and Communications in Medicine (DICOM) format to NifTI.

Figure 3:
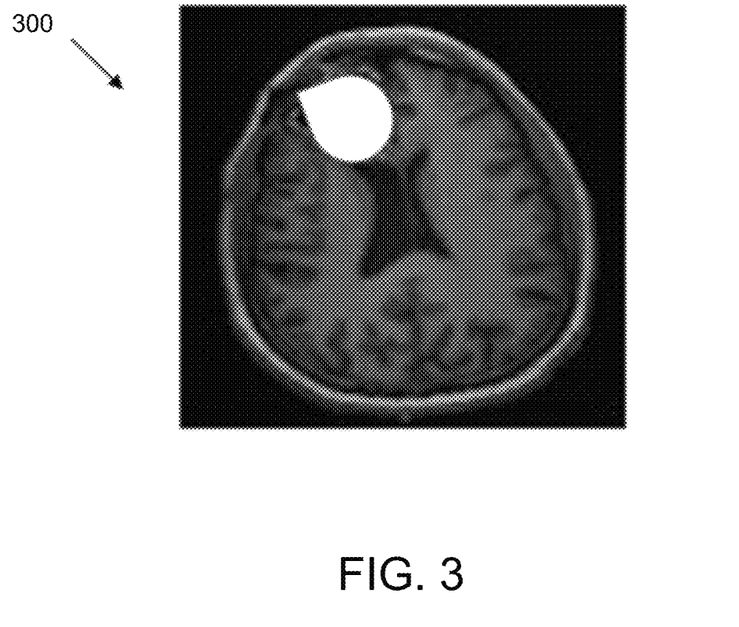
FIG. 3 depicts the MRI image of FIG. 2 with the abnormality masked out.

Process 100 continues in Step S3, which is masking of abnormal regions in the head. Step S3 is implemented only if a tumor or other abnormality (e.g., skull defects/flaps)

exists in the patient MRI images. In step S3, these abnormal regions are masked out as depicted in image 300 in FIG. 3. Optionally, the regions that are masked may extend beyond the tumor/abnormality if necessary so as to include all regions in which the normal structure of the brain has been significantly disturbed due to the presence of the tumor or other defects.

One way to accomplish this masking step is to use supervised segmentation to properly mark the abnormal head regions. During this step of the supervised segmentation, multiple types of abnormalities are labeled in order to reach the desired detail level of the final model as will be described hereinafter. The supervised segmentation may be performed in a semi-automatic manner using, for example, tools such as ITK-SNAP (see, e.g., Yushkevich et. al, Neuroimage, 31 1116-1128 (2006), which is incorporated herein by reference).

Alternatively, masking can be performed using automatic segmentation algorithms. For instance, Porz, et al. "Multimodal glioblastoma segmentation: man versus machine." Public Library of Science (PLOS) One, 9.5 (2014), teach a method for automatic segmentation of pre-operation MRI images. In some situations, manual corrections to the results of the automatic segmentation process may be required to ensure accurate masking of the tumor.

In some embodiments, the regions that are masked are determined manually. One way to accomplish this is to present the MRI data to a user, and ask the user to outline the tumor on the data. The data presented to the user may include structural MRI data (e.g., $T_1$, $T_2$ data). The different MRI modalities may be registered onto each other, and the user may be presented with the option to view any of the datasets and outline the tumor. The user may be asked to outline the tumor on a 3D volumetric representation of the MRI data, or the user may be given the option of viewing individual 2D slices of the data and marking the tumor boundary on each slice. Once the boundaries have been marked on each slice, the tumor within the anatomic volume can be found. In this case, the volume marked by the user would correspond to the tumor. In some situations, margins of a predefined width (e.g., 20 mm) are added to the tumor, and the resulting volume is used as the region-to-be-masked.

Note that when no tumor or other abnormality exists in the patient's MRI images (e.g., when the patient is healthy), step S3 is omitted.

For certain patients, the results of the segmentation will reveal that the tumor is not homogeneous, in which case the tumor may also be segmented into several sub-regions so that such segmentation information can be used for more accurately planting the tumor back into the realistic head model after the deformation step as will be described in further detail herein. Examples of such sub-regions are active/enhancing tumor, necrotic regions, resection cavity, etc. Conventional automated segmentation algorithms may be used for detailed GBM segmentation. An example of a publicly available algorithm is the recent Brain Tumor Image Analysis (BraTumIA) software which distinguishes necrotic core, edema, non-enhancing tumor, and enhancing tumor while needing four different imaging modalities (T1, T1-contrast, T2-contrast, and FLAIR). Techniques which only need a T1 as input also exist. But regardless of any variations within the tumor, all regions of the tumor are masked out of the original patient image. In case skull defects are in the image, then these regions are segmented and masked out as well.

Note that while a variety of approaches for identifying the abnormal region in the image are described above, a wide variety of alternative approaches will be apparent to persons skilled in the relevant arts.

Figure 4:
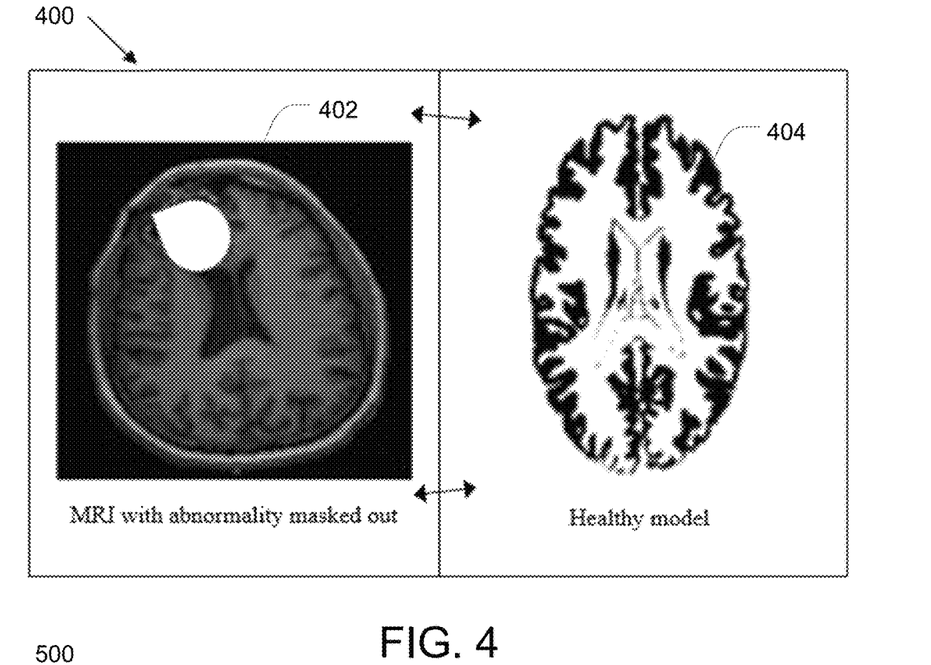
FIG. 4 depicts the normalization/registration process that generates the mapping and inverse mapping between FIG. 3 and a model deformable template of a healthy individual.

Process 100 continues in step S4, which is Spatial Normalization/Registration. In step S4, a mapping that warps the current set of MRI images for a given patient into the standard space of the template model is identified. FIG. 4 depicts the normalization/registration process 400 that generates the mapping and inverse mapping between a patient MRI image 402 (with a masked-out abnormality) and the deformable model template 404 of a healthy individual. The inverse of this mapping is also identified (for use in step S5 below to map from the standard space to the space of the patient MRI set).

For example, one approach for generating this mapping is to register the patient MRI images to a standard coordinate space, such as the MNI space or the Talairach space. Image registration refers to spatial transformation of an image so that certain features of the image align with corresponding features in another image/space. This can be done by any known methods that will be apparent to persons skilled in the relevant arts, for example, by using readily available software packages including but not limited to FSL FLIRT, and SPM.

Notably, abnormal regions masked out in step S3 are omitted from the registration process. Ignoring the masked out regions during registration ensures that the registration is performed using only healthy regions of the head, which can be effectively mapped to the model TPMs that describe the probability that a specific voxel in the standard space belongs to a specific tissue type. Advantageously, omitting the abnormal regions improves the robustness of the registration process. In some embodiments, the TPMs are constructed in the model template space.

Alternatively, non-rigid registration algorithms (as described, for example, in Zhuang et. al, IEEE Transactions on Medical Imaging, 30 0278-0062 (2011), which is incorporated herein by reference and teaches an algorithm for image registration using mutual information) can be used to register the patient MRI images to either a standard coordinate space (e.g., a realistic model template of a healthy individual) or to a voxelized version of the corresponding segmented model template. Note that a variety of algorithms for mapping patient MRI images into a standard space are well known to persons skilled in the relevant arts. Moving in the opposite direction (i.e., from the standard space to the patient MRI images, as described below) will use the inverse of those same mappings.

The mappings described above are found for the points in the patient head that fall outside of the masked-out areas. The transformations in the region(s) that were masked out prior to registration can be estimated, for example, by interpolating the deformation map found in the rest of the head into these regions, or using any of a variety of alternative approaches that will be apparent to persons skilled in the relevant arts. In some embodiments, it may not be necessary to find a transformation for the region(s) that were masked-out prior to registration. This is due to the fact that the areas of the deformable model template that correspond to the masked-out region contain information related to some "natural" structure (e.g., healthy tissue). Therefore, after the mappings described above are applied to the deformable model template for the points that fall outside of the masked-out regions, the deformed model template already includes some model data in these regions since the "natural" structure is maintained in these regions. For example, if a sphere is masked-out from the left hemisphere in patient images and the mappings are applied to the deformable model template only for the points that fall outside of the sphere, the contents of the sphere in the left hemisphere of the deformed model template will resemble some natural structure.

In some embodiments, model TPMs are used to find the mapping from the standard space to the patient space. In some embodiments, the model TPMs may be derived from the MRI dataset from which the deformable template was derived. Using TPMs derived from this MRI dataset may lead to a more accurate representation of the patient in the final model, than when using other TPMs. The reason for this is as follows. TPMs describe the probability of a voxel in a standard space belonging to each tissue type. Generally, TPMs are derived from multiple MRIs of different subjects. Thus, TPMs represent the probability of a voxel belonging to each tissue type throughout a population of individuals. This implies that when performing registration using TPMs derived from multiple individuals, the output mapping represents a mapping into some representative space that by definition smooths out anatomical variation between the individuals from which the TPMs were derived. However, when creating patient models by deforming a head model of a healthy individual, it may be desirable that the mapping calculated when registering the patient MRI onto the TPMs captures the anatomical features of the healthy head model with as much accuracy as possible. This accuracy ensures that when the deformable template is later deformed into the patient space in step S5 below, the resulting model resembles the patient with as much accuracy as possible. Hence, it is desirable that the TPMs onto which the registration in step S4 is performed represent the individual from which the healthy head model was derived, as opposed to a population of individuals from which TPMs are typically derived.

One approach for creating TPMs that represent the healthy individual from which the deformable model template was derived is to simultaneously register and segment MRI images of the healthy individual using an existing set of generic TPMs (e.g., TPMs built in a standard space using data of multiple individuals). An example of an algorithm that accomplishes this is the unified segmentation algorithm by Ashburner and Friston ("Unified segmentation." Neuroimage 26.3 2005) which is implemented in SPM 8.0 toolbox described above. Outputs from this process include probability maps describing the probability that a voxel (of the MRI images registered to the standard space) belongs to a specific tissue type. The number of probability maps generated in this process is equal to the number of tissue types in the model (typically 6), and each voxel in a map is assigned a value from 0 to 1 which indicates the probability that the voxel belongs to a specific tissue type. By definition, these probability maps are TPMs that represent the healthy individual from whom the healthy head model (deformable template) was derived.

In some cases, manual corrections are made to the TPMs to obtain a better representation of the deformable template. For instance, the probability maps of the skull and scalp could be modified to enhance the boundaries of the skull or scalp. This may be done, for example, by manually assigning probability values to specific voxels such that the probability of that voxel to belong to one tissue types is close to 1, and the probability of it belonging to other tissue types is close to 0. A final step in creating TPMs from these probability maps is to apply a smoothing filter to the individual maps. Smoothing is important to allow adjustments to an MRI of any individual. The smoothing can be performed for instance using a Gaussian filter with a smoothing kernel of 4 mm×4 mm×4 mm FWHM (Full width half maximum).

Figure 5:
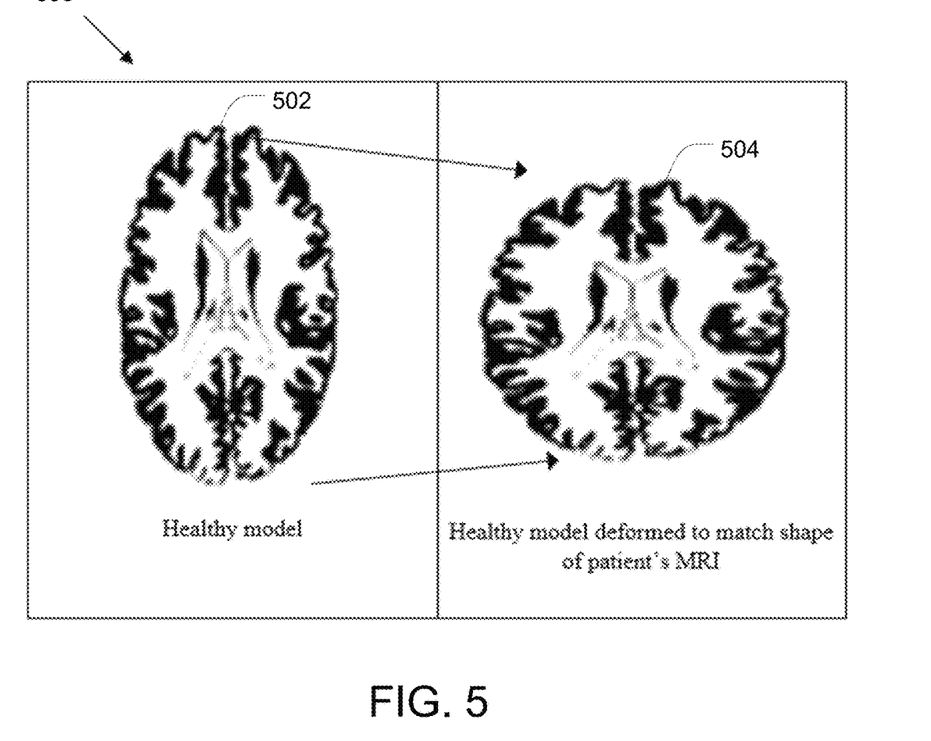
FIG. 5 depicts how the deformable template of FIG. 4 is deformed to match the shape of the patient's MRI image.

Process 100 continues in Step S5, which is Deforming/Warping the template into the desired space. In step S5, the inverse mapping found in step S4 is applied to the deformable model template to map the deformable model template into the coordinate system of the patient MRI images. FIG. 5 depicts the deforming/warping process 500 that applies the inverse mapping to a deformable model template 502 to obtain the warped model 504. In some embodiments, the inverse mapping applies a three-dimensional transformation to the deformable model template 502, thereby warping the deformable model template 502 to conform to patient-specific anatomical attributes.

It should be noted that prior to warping, the model template 502 is a model of a healthy reference individual's brain; and after warping, the warped model 504 will represent an approximation of what the patient's brain would look like if it were healthy. In other words, this step results in a model of a healthy individual that has been warped to fit into the head shown in the patient MRI images, but lacks a tumor. Notably, despite the fact that this warped model originates from a model template (instead of from each individual patient's head), it is still useful for analyzing the electrical fields that can be induced inside each individual patient's head.

The deformation in step S5 can be applied to a voxelized version of the model or to a meshed version of the model. In the voxelized version, each voxel indicates a tissue type (or tissue type probabilities) at the location of the coordinates of that voxel. In the meshed version, each mesh defines a boundary between different tissue types, and the deformation is applied to these meshes in the deformable model template. In some embodiments, a binary image of each tissue type is created, and each resulting binary image is deformed separately.

Optionally, any holes that may appear in the deformed image of a tissue type may be assigned to one of the tissue types that appear in that image. An example of a procedure designed to assign tissue types to holes that appear between binary masks can be found in Timmons, et al. "End-to-end workflow for finite element analysis of tumor treating fields in glioblastomas," Physics in Medicine & Biology, 62.21 (2017), where using the software ScanIP, a Gaussian filter function smooths the boundaries between masks to avoid convergence issues. Cavities in the mask are filled, and islands above a threshold (which may vary with tissue type) are removed. The current mask is duplicated and then dilated (by one to three voxels, depending on the tissue mask) and Boolean added to the next mask on all slices. Any of a variety of alternative approaches for filling holes that appear in the deformed image may also be used.

After the formation of the images for each individual tissue type, all the binary images are combined into a single image representing a segmented image of the deformed head model.

In cases where a voxel in the combined model is assigned to more than one tissue type, a heuristic logic may be used to determine the tissue type in the final image. For instance, the logic may state that all voxels where grey and white matter overlap in the combined model are assigned to white matter only, or vice versa.

In embodiments where the model template includes TPMs (i.e., each tissue in the model template is represented by a 3D matrix describing the probability that each voxel belongs to a specific tissue type), the TPMs are deformed, and the deformed TPMs are combined into a final model such that each voxel in the combined model is assigned a tissue type based on some heuristic logic. For instance, each voxel is assigned to the tissue type which has the highest probability of occupying that voxel.

In some embodiments, the probability assigned by different TPMs to each voxel is used to determine the combination of the conductivity properties in the created voxelized model. In other words, it is assumed that the voxel does not necessarily contain a certain tissue type, and the final conductivity is assigned to the voxel as a weighted sum of the conductivities of all tissue types, with the weights derived from the probability values assigned to each tissue type in that voxel.

In some embodiments, conductivity values are assigned to the tissue maps by additionally incorporating information obtained from MRI imaging techniques such as DTI or Wept, which are known to provide information on tissue conductivity as disclosed, for example, in U.S. application Ser. No. 15/336,660 (published as US2017/0120041), which is incorporated herein by reference in its entirety. This information could be incorporated into the model, for instance, by assigning conductivity to each voxel based on the weighted average of the model-derived conductivity and the Wept/DTI derived conductivity.

Figure 6:
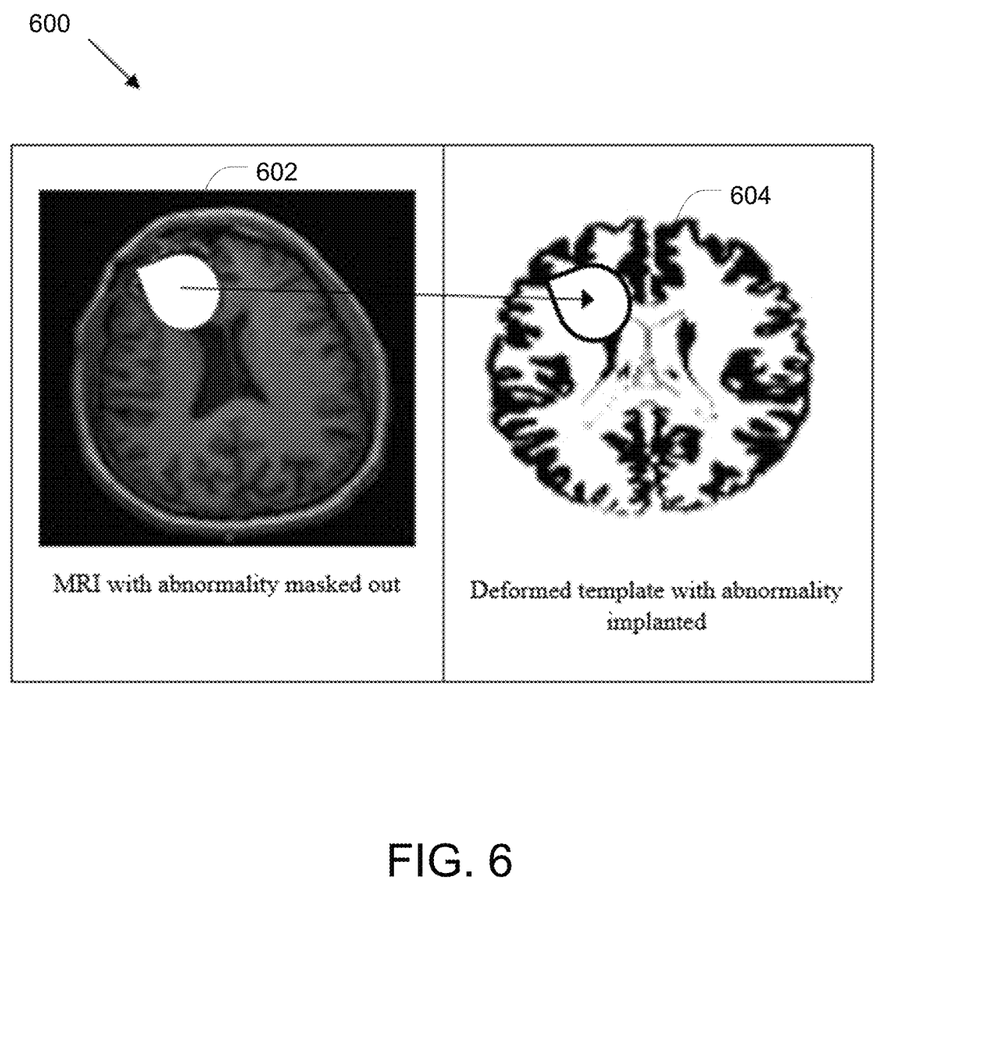
FIG. 6 depicts implanting the abnormality back into the deformed model.

Process 100 continues in Step S6, which is planting the abnormality back into the deformed template. In step S6, the deformed template is edited so that each voxel of the template that corresponds to the masked region found in step S3 is assigned to an abnormal tissue type (e.g., the tumor or surrounding region). FIG. 6 depicts this process 600 where an abnormality identified in the patient image 602 is implanted in a deformed model template 604. In some embodiments, the planting is performed by assigning tissue types in each of the abnormal regions according to the segmentation performed in step S3. More specifically, the tissue type assigned to each point in the abnormal region after deformation is based on the tissue type identified for a corresponding point in the segmentation in step S3 before deformation. Accordingly, if the segmentation in step S3 identifies more than one tissue type in the abnormal region, then there may be more than one tissue type assigned to the abnormal region after deformation. In alternative embodiments, the planting may be performed by assigning a default abnormal tissue type to the abnormal region after deformation. In other alternative embodiments, the planting may be performed by having a user manually assign a tissue type to the points in the abnormal region.

Process 100 continues in Step S7, which is model creation. In the modeling step (S7), electrical properties such as conductivity and permittivity are assigned to the various tissue types. Note that the tissue types are ordinarily obtained from the deformed template. However, a tissue type corresponding to tumor tissue will be assigned to each voxel that corresponds to the implanted abnormality. Models of electrodes (or transducer arrays) are placed on the model skin, and suitable boundary conditions are applied. In some embodiments, the modeling step S7 assumes that each tissue type is homogeneous and therefore a single value for the electrical property is assigned to each tissue type (as described, for example, in Miranda et. al., Physics in Medicine and Biology, 59, 4137-4147 (2014), Wenger et. al., Physics in Medicine and Biology, 60 7339-7357 (2015), and Wenger et. al., International Journal of Radiation Oncology•Biology•Physics, 941137-43 (2016)). In other models, the conductivity in each voxel is assigned from DTI or DWI images acquired during the image acquisition step. DTI assigns anisotropic electric properties (a 3×3 tensor) to each voxel, whereas DWI assigns isotropic conductivity (a scalar) to each voxel. Finally, the model is divided into volume elements, for example, by voxelizing or alternatively by volume meshing.

Process 100 continues in Step S8. After the head model is created and the model electrodes have been added to the head model, a simulation is run in step S8. This simulation finds an optimal electrode array layout by solving for the corresponding induced electric field using an appropriate numerical technique including but not limited to finite elements methods or finite differences methods.

Optimization of electrode array layouts means finding the array layout that optimizes the electric field within the diseased regions of the patient's brain (tumor). This optimization may be implemented over the volume targeted for treatment (target volume) within the realistic head model by automatically placing transducer arrays and setting boundary conditions on the realistic head model; calculating the electric field that develops within the realistic head model once arrays have been placed on the realistic head model and boundary conditions applied; and running an optimization algorithm to find the layout that yields optimal electric field distributions within the target volume. Although a variety of alternative approaches may be used, one example for implementing these four steps is provided below.

The position and orientation of the arrays on the realistic head model may be automatically calculated for a given iteration. Each transducer array used for the delivery of TTFields in the Optune™ device comprises a set of ceramic disk electrodes, which are coupled to the patient's head through a layer of medical gel. When placing arrays on real patients, the disks naturally align parallel to the skin, and good electrical contact between the arrays and the skin occurs because the medical gel deforms to match the body's contours. However, virtual models are made of rigidly defined geometries. Therefore, placing the arrays on the model requires an accurate method for finding the orientation and contour of the model surface at the positions where the arrays are to be placed, as well as finding the thickness/ geometry of the gel that is necessary to ensure good contact of the model arrays with the realistic patient model. In order to enable fully automated optimization of field distributions these calculations have to be performed automatically.

A variety of algorithms to perform this task may be used. The steps of one such algorithm devised for this purpose are set forth below.

a. Define the position at which the central point of the transducer array will be placed on the model head. The position could be defined by a user or as one of the steps in the field optimization algorithm.

b. Using the input from step (a) in conjunction with knowledge about the geometry of the disks and how the disks are arranged in the array, calculate the approximate positions of the centers of all disks in the transducer array within the model.

c. Calculate the orientations of the surface of the realistic model at the positions where the disks are to be placed. The calculation is performed by finding all points on the computational phantom skin that are within a distance of one disk radius from the designated center of the disk. The coordinates of these points are arranged into the columns of a matrix, and singular value decomposition performed on the matrix. The normal to the model skin is then the eigenvector that corresponds to the smallest eigenvalue found.

d. For each disk in the transducer array: calculate the thickness of the medical gel that is required to ensure good contact between the disks and the patient's body. This is done by finding the parameters for a cylinder with its height oriented parallel to the skin surface normal. The cylinder is defined with a radius equal to the radius of the disks, and its height set to extend a pre-determined amount (this is a pre-determined constant) beyond the points on the skin used to find the normal. This results in a cylinder that extends at-least the pre-determined amount out from the phantom surface.

e. On the model, create the cylinders described in (d).

f. Through binary logical operations (e.g., subtract head from cylinder) remove from the model the regions of the cylinder that protrude into the realistic model of the patient. The resulting "truncated cylinders" represent the medical gel associated with the transducer arrays.

g. On the outer side of the "truncated cylinders" place disks that represent the ceramic disks of the transducer arrays.

Then, the electric field distribution is calculated within the head model for the given iteration. Once the head phantom is constructed and the transducer arrays (i.e., the electrode arrays) that will be used to apply the fields are placed on the realistic head model, then a volume mesh, suitable for finite element method analysis, can be created. Next, boundary conditions can be applied to the model. Examples of boundary conditions that might be used include Dirichlet boundary (constant voltage) conditions on the transducer arrays, Neumann boundary conditions on the transducer arrays (constant current), or floating potential boundary condition that set the potential at that boundary so that the integral of the normal component of the current density is equal to a specified amplitude. The model can then be solved with a suitable finite element solver (e.g., a low frequency quasi-static electromagnetic solver) or alternatively with finite difference algorithms. The meshing, imposing of boundary conditions, and solving of the model can be performed with existing software packages such as Sim4Life, Comsol Multiphysics, Ansys, or Matlab. Alternatively, custom computer code that realizes the finite element (or finite difference) algorithms could be written. This code could utilize existing software resources such as C-Gal (for creating meshes), or FREEFEM++ (software written in C++ for rapid testing and finite element simulations). The final solution of the model will be a dataset that describes the electric field distribution or related quantities such as electric potential within the computational phantom for the given iteration. In some embodiments, the model is voxel-based (i.e., it comprises box-shaped volume elements). In these embodiments, Finite Differences Time Domain (FDTD) algorithms may be used to solve the model, for example, using the quasi-electrostatic solver associated with the "Sim4Life" software package from ZMT Zurich MedTech AG.

Then, an optimization algorithm is used to find the array layout that optimizes the electric field delivery to the diseased regions of the patient's brain (tumor) for both application directions (LR and AP). The optimization algorithm will utilize the method for automatic array placement and the method for solving the electric field within the head model in a well-defined sequence in order to find the optimal array layout. The optimal layout will be the layout that maximizes or minimizes some target function of the electric field in the diseased regions of the brain, considering both directions at which the electric field is applied. This target function may be for instance the maximum intensity within the diseased region or the average intensity within the diseased region. It also possible to define other target functions.

There are a number of approaches that could be used to find the optimal array layouts for patients, three of which are described below. One optimization approach is an exhaustive search. In this approach the optimizer will include a bank with a finite number of array layouts that should be tested. The optimizer performs simulations of all array layouts in the bank and picks the array layouts that yield the optimal field intensities in the tumor (the optimal layout is the layout in the bank that yields the highest (or lowest) value for the optimization target function, e.g., the electric field strength delivered to the tumor).

Another optimization approach is an iterative search. This approach covers the use of algorithm such as minimum-descent optimization methods and simplex search optimization. Using this approach, the algorithm iteratively tests different array layouts on the head and calculates the target function for electric field in the tumor for each layout. At each iteration, the algorithm automatically picks the configuration to test based on the results of the previous iteration. The algorithm is designed to converge so that it maximizes (or minimizes) the defined target function for the field in the tumor.

Yet another optimization approach is based on placing a dipole at the center of the tumor in the model. This approach differs from the other two approaches, as it does not rely on solving field intensity for different array layouts. Rather, the optimal position for the arrays is found by placing a dipole aligned with the direction of the expected field at the center of the tumor in the model, and solving the electromagnetic potential. The regions on the scalp where the electric potential (or possibly electric field) is maximal will be the positions where the arrays are placed. The logic of this method is that the dipole will generate an electric field that is maximal at the tumor center. By reciprocity, if we were able to generate the field/voltage on the scalp that the calculation yielded, then we would expect to obtain a field distribution that is maximal at the tumor center (where the dipole was placed). The closest we can practically get to this with our current system is to place the arrays in the regions where the potential induced by the dipole on the scalp is maximal.

Note that alternative optimization schemes can be used to find an array layout that optimizes the electric field within diseased regions of the brain. For example, algorithms that combine the various approaches mentioned above. As an example of how these approaches may be combined, consider an algorithm in combining the third approach discussed above (i.e., positioning the dipole at the center of the tumor in the model) with the second approach (i.e., the iterative search). With this combination, an array layout is initially found using the dipole at the center of the tumor approach. This array layout is used as input to an iterative search that finds the optimal layout.

Once the layout that optimizes the electric field within the diseased regions of the patient's brain has been determined (e.g., using any of the approaches explained herein, or an appropriate alternative approach), the electrodes are positioned in the determined positions. AC voltages are then applied to the electrodes (e.g., as described in U.S. Pat. No. 7,565,205, which is incorporated herein by reference) to treat the disease.

Figure 7:
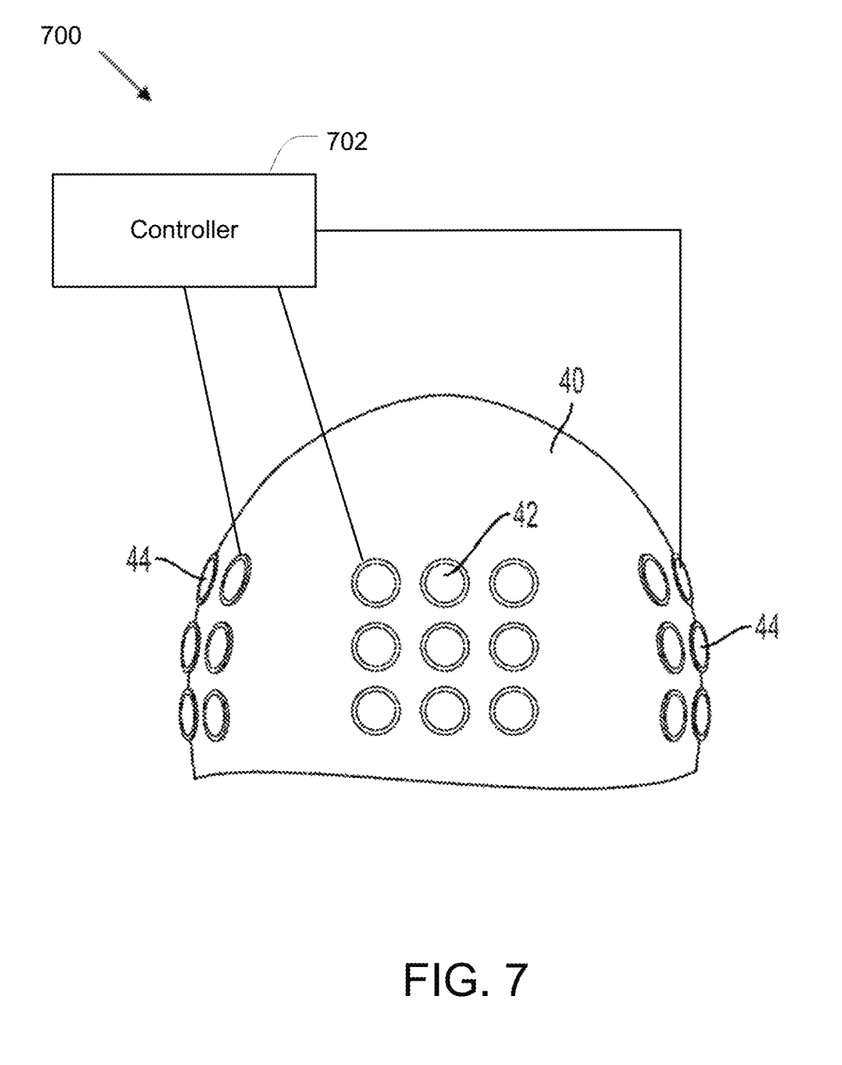
FIG. 7 depicts a system for electrotherapeutic treatment according to one embodiment.

FIG. 7 depicts an example system 700 for electrotherapeutic treatment that may be used after the positions of the electrodes have been optimized as described herein. System 700 includes a controller 702 that applies TTFfields to a patient by applying voltages to capacitively coupled transducer arrays 42, 44 that are affixed to the patient's scalp 40 at the determined positions. Note that the front view of the scalp 40 is depicted in FIG. 7 and only three of the four patches of electrodes are visible in the figure and that neither the eyes nor the ears are represented.

Optionally, the system can be designed to work with multiple model templates. In this case, an additional step S3.5 is implemented subsequent to step S3 and prior to step S4. In step S3.5, the resemblance of the patient MRI images to each of a plurality of templates is first measured (using, for example, a measure of correlation or mutual information). The deformable template that most closely resembles the patient MRI images is selected and used in all subsequent steps. Alternatively, in some embodiments, selection of the deformable template that most closely resembles the patient Mill images may be performed after registering patient images to a standard space at step S4 and prior to step S5. In these embodiments, the deformable template that most closely resembles the patient MRI images is used in all steps subsequent to S4.

Optionally, the system may be configured as a learning system in which each realistic head model that is created using the process described above serves as a deformable template for future models. Both the deformed healthy model created in step S5 and the resulting model that includes defects (created in step S6) could be added to the database. If a patient's MRI images in the original image stack resemble a stored template of a brain with a tumor to a close enough degree, then it is possible to create a model representing the patient MRI images by measuring deformations on the previously stored template.

Finally, while the concepts set forth herein are discussed in the context of an MRI image of a patient's head, the same principles may be applied to other portions of a patient's body and/or imaging modalities other than MRI.

FIG. 8 is a flowchart 800 of a method for optimizing the position of electrodes that will subsequently be used to perform electrotherapeutic treatment by creating a realistic head model of a patient using a deformable template. The electrotherapeutic treatment may be TDCS, TMS, or TTFields.

At S10 one or more 3D images of a body area of a patient are received. The 3D images may be MRI images, CT images, or images in any other modalities known in the art. The body area may be the patient's head, or any other body area. Optionally, the images may be pre-processed using any of the approaches described herein (for example, as described herein with reference to step S2 of FIG. 1).

At S20 portions of the image that correspond to abnormal tissue are identified. For example, when the body area is the head of a patient, such portions may correspond to a tumor or a skull abnormality. The abnormality may be identified manually, automatically, or semi-automatically, according to any of the methods described herein or according to any other appropriate methods that will be apparent to persons skilled in the relevant arts. In some embodiments, the portions of the image that correspond to the abnormal tissue are identified by segmentation of the image.

At S30 a data set is generated to correspond to the image with the abnormal tissue masked out. This may be accomplished, for example, by masking out the abnormal tissue includes ignoring the abnormal regions in the registration process described in S50 below. In some embodiments, masking out the abnormal region is implemented by flagging data points in this region and excluding all flagged data points during the registration process described in S50 below.

At S40 a model template that specifies positions of a plurality of tissue types in a healthy version of the body area of the patient is retrieved. For example, when the body area is the head of a patient and the abnormal tissue corresponds to a tumor in the head of the patient, the model template corresponds to the head of a healthy individual and lacks any tumors. In some embodiments, the model template may be selected from multiple existing model templates based on similarities between the image and each of the multiple model templates. For example, a measure of similarity such as mutual information or a distance may be determined between the patient data set (derived by masking out abnormalities in the patient image) and each one of several model templates, and the model template that is most similar to the patient data set (e.g., has the least distance or the most mutual information) may be selected accordingly. In some embodiments, the model template may include TPMs, and the TPMs may correspond to the same healthy individual from whom the model template has been derived (and derived from images of the healthy individual) or to multiple individuals.

At S50 the model template is deformed in space so that features in the deformed model template line up with corresponding features in the data set. In some embodiments, the model template is deformed by determining a mapping that maps the data set to a coordinate space of the model template; and applying an inverse of the mapping to the model template. In some embodiments, the mapping may be determined by registering the dataset to a coordinate space of the model template. That is, the mapping warps the dataset to the model template. Hence, the inverse of the mapping warps the model template to the data set and thereby provides a realistic model for the patient if the patient had no abnormalities. In some embodiments, the mapping from the data set to the model template is determined for points in the data set that fall outside of the masked-out portion. In embodiments where the model template includes TPMS, the mapping maps the data set to the TPMs, and the inverse of the mapping is applied to each one of the TPMs and the inverse-mapped TPMs are combined into a segmented image comprising the deformed model template.

At S60 portions of the deformed model template that correspond to the masked-out portion of the data set are modified so that the modified portions represent the abnormal tissue. The modification may be performed according to the information obtained during the identification of the abnormal portions in S20. For example, one or more abnormal tissue types identified in S20 may be assigned to corresponding portions in the deformed model template. Alternatively, a pre-determined generic tissue type may be assigned to the masked-out portion.

At S70 a model of electrical properties of tissues in the body area is generated based on (a) the positions of the plurality of tissue types in the deformed and modified model template and (b) the position of the abnormal tissue in the deformed and modified model template. The electrical properties may be electrical conductivity, electrical resistivity, or any other electrical property pertinent to electrotherapeutic treatment of the body area. In some embodiments, for example, a different electrical property value may be assigned to each tissue type according to a previously populated look-up table.

At S80 an electrode placement layout that maximizes field strength in at least a portion of the abnormal tissue is determined by using the model of electrical properties to simulate electromagnetic field distributions in the body area caused by simulated electrodes placed at a plurality of different sets of candidate positions respective to the body area, and selecting one of the sets. In some embodiments, the electrode placement layout is determined by applying a boundary condition to the simulated electrodes in each one of at least two electrode placement layouts; solving a field distribution in the body area for each one of the at least two electrode placement layouts; and choosing the electrode placement layout that yields the strongest field within the abnormal region. The boundary condition may correspond, for example, to voltages applied to the simulated electrodes. In some embodiments, the field distribution is solved using a numerical technique such as a finite elements method or a finite differences method.

At S90 the determined electrode placement layout is output for subsequent use as a guide for placing electrodes respective to the body area of the patient prior to use of the electrodes for electrotherapeutic treatment (e.g. TTFields).

Models built in this manner could also be used for other applications in which calculating electric field and or electric current distributions within the head may be useful. These applications include, but are not limited to: direct and alternating current trans-cranial stimulation; simulations of implanted stimulatory electrode field maps; planning placement of implanted stimulatory electrodes; and source localization in electroencephalogram (EEG).

Finally, although this application describes methods for optimizing array layouts on the head, the same steps may be used for optimizing array layouts at other body regions (including but not limited to the thorax or abdomen).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method for improving treatment of a tumor using Tumor Treating Fields (TTFields), the method comprising:
   receiving, by a processor of a computer system, a three-dimensional image of a body area of a patient;
   identifying portions of the image that correspond to abnormal tissue;
   generating a data set corresponding to the image with the abnormal tissue masked out;
   retrieving a model template from a memory device of the computer system, the model template comprising tissue probability maps that specify positions of a plurality of tissue types in a corresponding body area of a healthy individual that is distinct from the patient;
   deforming the model template in space so that features in the deformed model template line up with corresponding features in the data set;
   modifying portions of the deformed model template that correspond to the masked-out portion of the data set so that the modified portions represent the abnormal tissue;
   generating a model of electrical properties of tissues in the body area based on (a) the positions of the plurality of tissue types in the deformed and modified model template and (b) a position of the abnormal tissue in the deformed and modified model template;
   determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets;
   placing the electrodes respective to the body area of the patient based on the determined electrode placement layout; and
   using the placed electrodes to apply TTFields to the body area.

2. An electrotherapeutic treatment device comprising a processor configured to execute instructions stored in one or more memory devices to perform an electrotherapeutic treatment comprising:
   receiving, by the processor, a three-dimensional image of a body area of a patient;
   identifying portions of the image that correspond to abnormal tissue;
   generating a data set corresponding to the image with the abnormal tissue masked out;
   retrieving a model template from the one or more memory devices, wherein the model template specifies positions of a plurality of tissue types in a corresponding body area of a healthy individual that is distinct from the patient;
   deforming the model template in space so that features in the deformed model template line up with corresponding features in the data set;
   modifying portions of the deformed model template that correspond to the masked-out portion of the data set so that the modified portions represent the abnormal tissue;
   generating a model of electrical properties of tissues in the body area based on (a) the positions of the plurality of tissue types in the deformed and modified model template and (b) a position of the abnormal tissue in the deformed and modified model template;
   determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets; and
   outputting the determined electrode placement layout for subsequent use as a guide for placing electrodes respective to the body area of the patient prior to use of the electrodes for electrotherapeutic treatment.

3. A method for improving an electrotherapeutic treatment comprising:
   receiving, by a processor of a computer system, a three-dimensional image of a body area of a patient;
   identifying portions of the image that correspond to abnormal tissue;
   generating a data set corresponding to the image with the abnormal tissue masked out;
   retrieving a model template from a memory device of the computer system, wherein the model template specifies positions of a plurality of tissue types in a corresponding body area of a healthy individual that is distinct from the patient;

deforming the model template in space so that features in the deformed model template line up with corresponding features in the data set;

modifying portions of the deformed model template that correspond to the masked-out portion of the data set so that the modified portions represent the abnormal tissue;

generating a model of electrical properties of tissues in the body area based on (a) the positions of the plurality of tissue types in the deformed and modified model template and (b) a position of the abnormal tissue in the deformed and modified model template;

determining an electrode placement layout that maximizes field strength in at least a portion of the abnormal tissue by using the model of electrical properties to simulate electromagnetic field distributions in the body area caused by simulated electrodes placed at a plurality of different sets of candidate positions respective to the body area, and selecting one of the sets; and outputting the determined electrode placement layout for subsequent use as a guide for placing electrodes respective to the body area of the patient prior to use of the electrodes for electrotherapeutic treatment.

4. The method of claim 3, wherein the identifying of the portions of the image that correspond to the abnormal tissue comprises performing segmentation of the image.

5. The method of claim 3, wherein the model of electrical properties of tissues comprises a model of electrical conductivity or resistivity.

6. The method of claim 3, wherein the image comprises an MRI image, or a CT image.

7. The method of claim 3, wherein the body area comprises a head of the patient.

8. The method of claim 3, wherein the portions of the image that correspond to the abnormal tissue correspond to a tumor.

9. The method of claim 3, wherein the electrotherapeutic treatment comprises Tumor Treating Fields (TTFields).

10. The method of claim 3, wherein the model template is selected from a plurality of model templates based on similarities between the image and each of the model templates.

11. The method of claim 3, further comprising:
placing the electrodes respective to the body area of the patient based on the determined electrode placement layout; and
using the electrodes to apply TTFields to the body area.

12. The method of claim 3, wherein the determining of the electrode placement layout comprises:

applying a boundary condition to the simulated electrodes in each one of at least two electrode placement layouts;
solving a field distribution in the body area for each one of the at least two electrode placement layouts; and
choosing the electrode placement layout that yields the strongest field within the abnormal tissue.

13. The method of claim 12, wherein the boundary condition corresponds to voltages or currents applied to the simulated electrodes.

14. The method of claim 3, wherein the deforming of the model template comprises:
determining a mapping that maps the data set to a coordinate space of the model template; and
applying an inverse of the mapping to the model template.

15. The method of claim 14, wherein the mapping is determined for points in the data set that fall outside of the masked-out portion.

16. The method of claim 14, wherein the model template comprises tissue probability maps, wherein the mapping maps the data set to the tissue probability maps.

17. The method of claim 16, wherein the tissue probability maps are existing tissue probability maps derived from images of multiple individuals.

18. The method of claim 16, wherein the tissue probability maps are derived from images of the healthy individual from whom the model template has been derived.

19. The method of claim 18, wherein the tissue probability maps are derived by simultaneously registering and segmenting the images of the healthy individual using existing tissue probability maps, and wherein the existing tissue probability maps are derived from images of multiple individuals.

20. The method of claim 16, wherein the inverse of the mapping is applied to each one of the tissue probability maps, wherein the inverse-mapped tissue probability maps are combined into a segmented image comprising the deformed model template.

21. The method of claim 20, wherein combining the inverse-mapped tissue probability maps includes assigning to each voxel the tissue type which has the highest probability of occupying that voxel across the inverse-mapped tissue probability maps.

22. The method of claim 20, wherein combining the inverse-mapped tissue probability maps includes using a look-up table to assign a tissue type to each voxel that is assigned more than one tissue type across the inverse-mapped tissue probability maps.

* * * * *